(12) United States Patent
Frielinghaus et al.

(10) Patent No.: US 11,067,498 B2
(45) Date of Patent: Jul. 20, 2021

(54) FOOD PREPARATION AND ANALYZING DEVICE

(71) Applicant: Vorwerk & Co. Interholding GmbH, Wuppertal (DE)

(72) Inventors: Robert Frielinghaus, Bochum (DE); Hendrik Koetz, Wetter (DE)

(73) Assignee: Vorwerk & Co. Interholding GmbH

( * ) Notice: Subject to any disclaimer, the term of this patent is extended or adjusted under 35 U.S.C. 154(b) by 0 days.

(21) Appl. No.: 16/293,092

(22) Filed: Mar. 5, 2019

(65) Prior Publication Data

US 2019/0277754 A1 Sep. 12, 2019

(30) Foreign Application Priority Data

Mar. 6, 2018 (EP) .................................. 18160089

(51) Int. Cl.
*G01N 21/35* (2014.01)
*A23L 5/30* (2016.01)
(Continued)

(52) U.S. Cl.
CPC ................ *G01N 21/35* (2013.01); *A23L 5/15* (2016.08); *A23L 5/30* (2016.08); *A47J 37/0664* (2013.01);
(Continued)

(58) Field of Classification Search
CPC ...... G01N 21/17; G01N 21/25; G01N 21/255; G01N 21/31; G01N 21/35; G01N 21/3554; G01N 21/3563; G01N 21/3577; G01N 21/3581; G01N 21/359; G01N 21/39; G01N 2021/3572; G01N 21/27; G01N 21/272; G01N 21/29; G01N 2021/3122; G01N 2021/3125; G01N 2021/3129; G01N 33/02; G01J 3/0208; G01J 3/0218; G01J 3/0248; G01J 3/0291; G01J 3/0256; B01F 15/00123; B01F 15/00207;
(Continued)

(56) References Cited

U.S. PATENT DOCUMENTS

| 6,418,805 B1 * | 7/2002 | Carney | ................. | A01D 41/127 |
| | | | | 374/142 |
| 7,075,645 B2 * | 7/2006 | Gehrlein | ................... | B01F 3/02 |
| | | | | 356/328 |

(Continued)

FOREIGN PATENT DOCUMENTS

DE 202008003977 U1 8/2009

OTHER PUBLICATIONS

Brian G. Osborne, Near-infrared Spectroscopy in Food Analysis, 2006, 14 pages.

*Primary Examiner* — Gordon J Stock, Jr
(74) *Attorney, Agent, or Firm* — Barnes & Thornburg LLP

(57) ABSTRACT

The present disclosure relates to a food preparation device. The device comprises a food preparation space, a heating element for heating a food in the food preparation space, and/or a tool for blending and/or chopping a food in the food preparation space. The device further comprises a spectrometer for analyzing a food associated with the device. The present disclosure further relates to a method for analyzing a food. In this way, a reproducible cooking result as well as an output of the nutritional values and the actual energy content of prepared food can be made possible.

9 Claims, 3 Drawing Sheets

Figure 2:
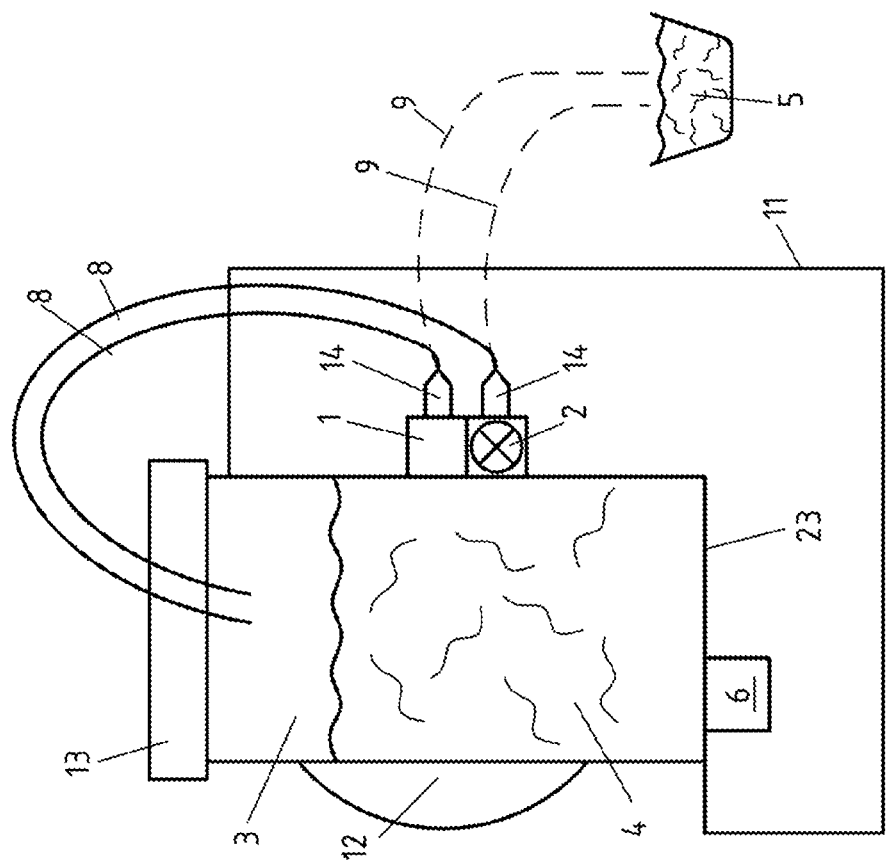

(51) Int. Cl.

| | |
|---|---|
| *A23L 5/10* | (2016.01) |
| *G01J 3/02* | (2006.01) |
| *G01N 21/3563* | (2014.01) |
| *G01N 21/3577* | (2014.01) |
| *G01N 21/359* | (2014.01) |
| *A47J 43/07* | (2006.01) |
| *A47J 37/06* | (2006.01) |
| *G01N 33/02* | (2006.01) |
| *A47J 43/046* | (2006.01) |
| *B01F 15/00* | (2006.01) |

(52) U.S. Cl.
CPC ......... *A47J 43/046* (2013.01); *A47J 43/0716* (2013.01); *B01F 15/00207* (2013.01); *G01J 3/0218* (2013.01); *G01J 3/0256* (2013.01); *G01N 21/359* (2013.01); *G01N 21/3563* (2013.01); *G01N 21/3577* (2013.01); *G01N 33/02* (2013.01); *G01J 3/0208* (2013.01); *G01J 3/0248* (2013.01); *G01N 2021/3572* (2013.01)

(58) Field of Classification Search
CPC ............ B01F 15/00214; B01F 15/0022; B01F 15/0024; B01F 15/00253; B01F 15/00259; B01F 15/00272; B01F 15/00285; B01F 15/00292; B01F 15/06; B01F 15/065; B01F 15/066; B01F 7/162; A47J 36/2483; A47J 36/2488; A47J 36/26; A47J 43/046; A47J 43/0716; A47J 43/0722; A47J 43/0705; A47J 43/0711; A47J 43/0727; A47J 31/521; A47J 31/525; A47J 37/0664; A47J 2202/00; A23L 5/30; A21C 1/145; A21C 1/146
See application file for complete search history.

(56) References Cited

U.S. PATENT DOCUMENTS

| | | | | |
|---|---|---|---|---|
| 8,623,441 | B2* | 1/2014 | McLaughlin | A47J 31/3614 426/433 |
| 8,629,399 | B2* | 1/2014 | Thomson | G01N 21/3577 250/339.09 |
| 9,488,632 | B2* | 11/2016 | Wang | G01N 33/12 |
| 9,540,701 | B2* | 1/2017 | Olesberg | G01N 21/39 |
| 10,254,264 | B2* | 4/2019 | Levanon | G01K 13/10 |
| 2002/0137216 | A1* | 9/2002 | Chen | G01N 21/359 436/20 |
| 2007/0188753 | A1* | 8/2007 | Merrill | G01P 3/44 356/326 |
| 2014/0320858 | A1 | 10/2014 | Goldring et al. | |
| 2015/0293067 | A1 | 10/2015 | Greene et al. | |
| 2017/0029761 | A1* | 2/2017 | Hoffmann-Petersen | C12M 41/48 |
| 2018/0059790 | A1* | 3/2018 | Kolar | A47J 43/27 |
| 2018/0239319 | A1* | 8/2018 | Abdoo | G05B 19/042 |
| 2019/0001288 | A1* | 1/2019 | Ciepiel | G06K 7/1413 |
| 2019/0056315 | A1* | 2/2019 | Kinrot | G01N 21/3151 |
| 2019/0125126 | A1* | 5/2019 | Cohen | A47J 36/32 |
| 2019/0254481 | A1* | 8/2019 | Frielinghaus | A47J 43/046 |
| 2019/0277757 | A1* | 9/2019 | Frielinghaus | B01F 15/00207 |
| 2019/0320850 | A1* | 10/2019 | Chen | G05B 15/02 |
| 2020/0042817 | A1* | 2/2020 | Gatto | G01N 21/31 |
| 2020/0069111 | A1* | 3/2020 | Eiter | F27D 21/02 |
| 2020/0182480 | A1* | 6/2020 | Bhogal | A23L 5/15 |
| 2021/0045582 | A1* | 2/2021 | Starmans | A47J 43/0716 |

* cited by examiner

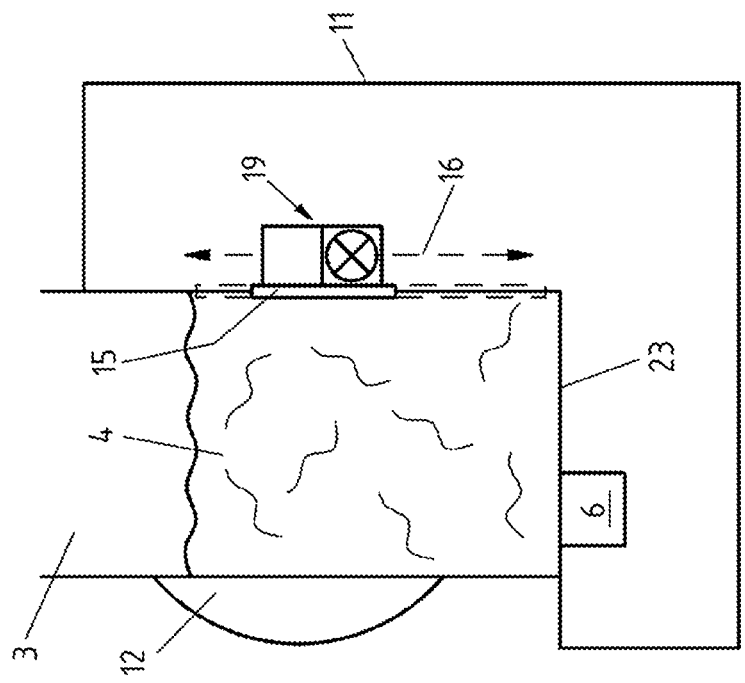
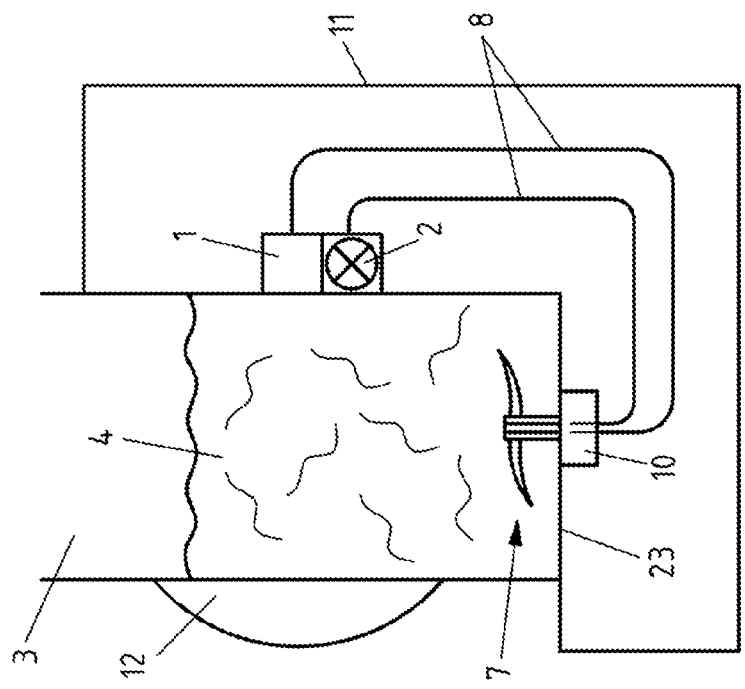

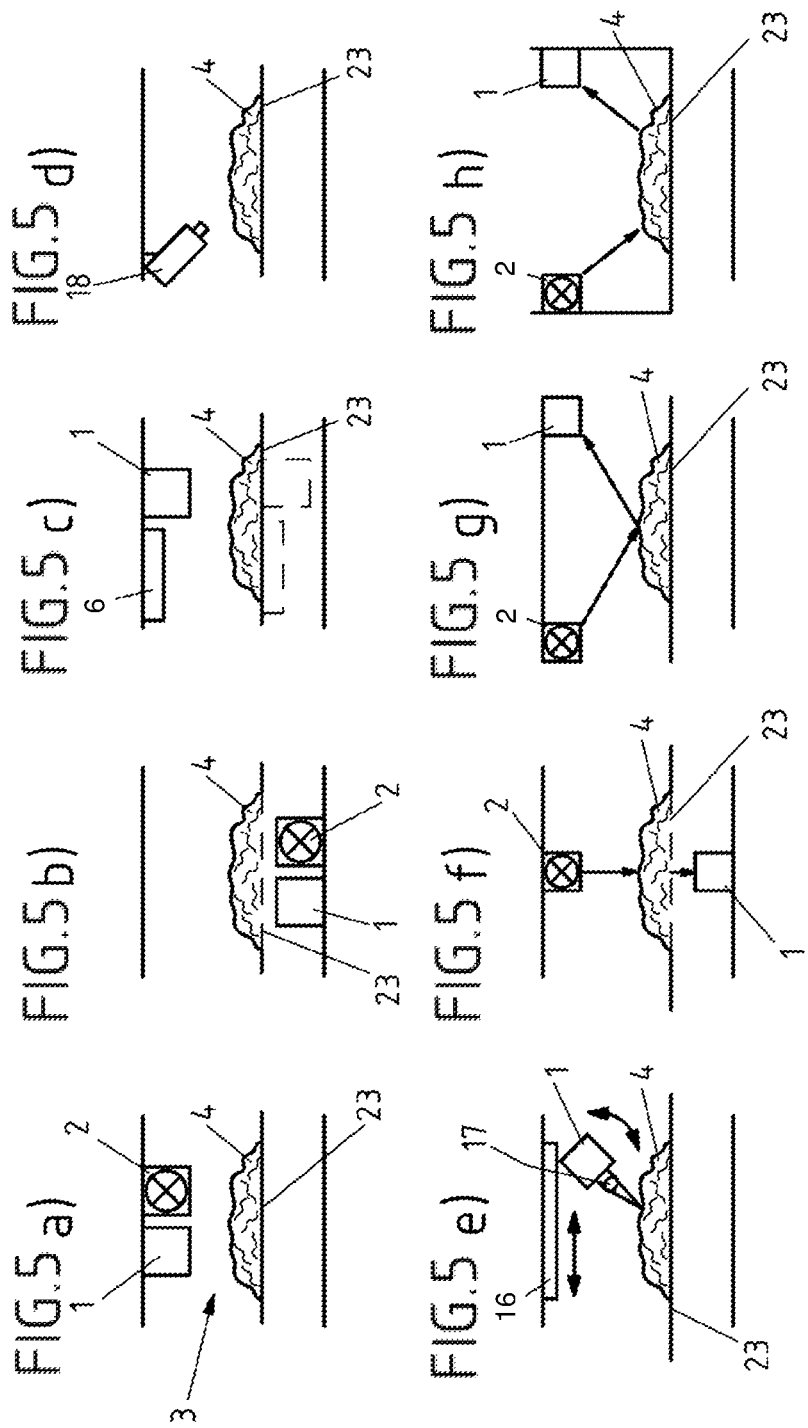

FOOD PREPARATION AND ANALYZING DEVICE

PRIORITY CLAIM

This application claims priority to European Application No. 18160089.1, filed Mar. 6, 2018, which application is hereby incorporated in its entirety herein.

FIELD OF THE DISCLOSURE

The present disclosure relates to a food preparation device, comprising a food preparation space and a heating element for heating a food in the food preparation space and/or a tool for blending and/or chopping a food in the food preparation space. The present disclosure further relates to a method.

BACKGROUND

When preparing food, the quality of the cooking result and the resulting nutritional values are dependent on the added food components and cooking parameters. Occasionally, therefore, considerable fluctuations usually occur with respect to the obtained quality of the cooking result and the resulting nutritional values.

Particularly in private households, an increasing interest in a healthy diet, high-quality foods and a precise knowledge of the nutritional values of self-prepared foods can be observed.

SUMMARY

The object of the present disclosure is to provide a food preparation device that has been developed further, as well as a method.

A food preparation device and a method according to the present disclosure serve for achieving the object. Advantageous embodiments are apparent from the description and drawings provided in this paper.

A food preparation device serves for achieving the object, which comprises a food preparation space and a heating element for heating a food in the food preparation space and/or a tool for blending and/or chopping a food in the food preparation space. According to the present disclosure, the food preparation device comprises a spectrometer for analyzing a food.

A food preparation device may be, for example, an oven, a cooking machine or an electric food processor, particularly with a tool for blending and/or chopping, which may optionally also be capable of heating.

"Food preparation space" means the space of container into which a food or food component is added and in which the food is being prepared. Preparing a food means processing by means of blending, chopping and/or heating. Food may be solid or liquid. A food component to be added, taken by itself, may also be a food, such as milk or drinking water.

A spectrometer is an, in particular optoelectronic, device which is capable of breaking down an electromagnetic radiation into its spectrum in such a way that the intensity of the radiation is measured as a function of the wavelength. Preferably, a spectrometer can be formed by a spectroscope and at least one radiation detector. A spectroscope is an optical device with which an electromagnetic radiation can be broken down into its spectrum, wherein the radiation is deflected in different ways depending on the wavelength. In particular, the spectroscope includes a spectroscopic splitting device, such as a grating, a prism or an interferometer. For example, white light can thus be split and the spectrum can be displayed on a screen in a rainbow-like manner. A radiation detector is a preferably electronic device for measuring the intensity of incident radiation. Preferably, the radiation detector is or comprises at least one photodiode which, when electromagnetic radiation is incident, outputs a measurement signal correlating with its intensity. Alternatively or additionally, the radiation detector may be a CCD sensor.

Main nutrients, food components or states of the food can preferably be identified by a so-called spectral fingerprint, i.e. by special wavelength-dependent intensity characteristics, e.g. predefined peaks at predefined wavelengths. Preferably, a food, property or a state can be associated by a comparison to stored reference values.

In a spectrometer formed from a spectroscope and a radiation detector, one or more radiation detector may in one embodiment be installed at predefined locations, towards which a portion of the measuring radiation with a certain wavelength is respectively diverted or directed. By means of the above-described setup, a food can thus be analyzed with a spectrometer with a particularly simple and compact structure. Alternatively or additionally, the spectrometer is configured such that the radiation detector is driven along the measuring radiation, which has been deflected according to its wavelength, so that, depending on the position, a measured intensity can be associated with the corresponding wavelength.

A food or a food component can be identified, its property can be detected or its condition can be determined by means of a food preparation device with a spectrometer for analyzing a food, namely prior to, during or subsequent to the preparation. So far, information of this kind was not known to a food preparation device. By using a spectrometer, information of this type can be made accessible to the food preparation device, and a particularly reproducible cooking result and particularly precise knowledge of the actually contained nutritional values can thus be obtained.

Based on the actually added food components prior to preparation and/or the actual state of the food during preparation, it is possible, for example, to monitor the process and optimize the preparation process by controlling individual cooking parameters, such as temperature and time, or by requesting the user to add a certain food component, such as sugar or water. Subsequent to preparation, main nutrients, i.e. carbohydrates, fat and protein can be determined and the energy content of the prepared food in kilocalories (kcal) can be calculated.

The use of a large number of individual sensors for detecting, in each case, a certain property or a certain state, such as the browning level by means of camera technology, alcohol concentrations by means of refractometers or water content by means of differential thermometry, may be dispensed with in this way, as well as a recipe-based estimation of the nutrients and the energy content using nutritional value and calorie tables. A food preparation device with the above-described functional capability, which has a particularly simple structure and can be manufactured with little effort, can thus be provided. Moreover, a high level of ease of use with little operating effort is thus obtained. Finally, operational safety, e.g. in the case of alcohol distillation, can be increased.

In one embodiment, a beam source for analyzing a food is provided. A beam source emits electromagnetic radiation for introducing energy into the food to be analyzed, also referred to as excitation radiation. A wide-band beam source, e.g. a Globar, a quartz halogen lamp or a high-pressure mercury lamp, with a spectrum known through reference measurement or calibration, is preferably provided. Alternatively or additionally, a diode laser is used as a beam source. A particularly precise analysis can be obtained using a beam source.

Preferably, the beam source emits infrared radiation. In particular, infrared radiation includes near infrared radiation (NIR) with a wavelength range of 780 nm to 1,400 nm, short-wavelength infrared radiation (SWIR) in the range of 1,400 nm to 3,000 nm, mid-wavelength infrared radiation (MWIR) in the range from 3,000 nm to 8,000 nm, long-wavelength infrared (LWIR) in the range from 8,000 to 15,000 nm and/or far infrared radiation (FIR) in the range from 15,000 nm to 1,000,000 nm. Preferably, a beam source emitting excitation radiation in the NIR range is provided. A food or food component can thus be analyzed particularly reliably.

For analyzing a food, the excitation radiation, i.e. photons, from the beam source is incident upon the food to be analyzed. There, the molecules are excited by this incident or introduced energy. Depending on the food, its properties or state, the excitation radiation is reflected, absorbed or transmitted by the food in certain fractions of the incident excitation radiation. In particular, the reflected radiation and/or the transmitted radiation are used as the measuring radiation to be captured by the radiation detector. Preferably, the reflected radiation is used as the measuring radiation. The term "measuring radiation" means the radiation from the food or a food component to be analyzed for analyzing the food.

In one embodiment an optical fiber is provided for guiding a measuring radiation from a food to the spectrometer and/or guiding an excitation radiation from the beam source to a food. An optical fiber is capable of guiding electromagnetic radiation, particularly in the NIR range. The optical fiber, which is preferably made from glass or plastic, permits bending. Due to the use of an optical fiber, the beam source and/or the radiation detector may thus be disposed or installed at any position in or on the food preparation device. Preferably, a main device includes the beam source and/or radiation detector for a compact integration into the food preparation device. Alternatively or additionally, a separate container with the food preparation space which, however, can be electrically connected to the main device, may also include the beam source and/or radiation detector.

In one embodiment, the optical fiber, in particular of the beam source and/or radiation detector, extends through an opening in a container with the food preparation space or in a lid for the food preparation space. In this way, the food can be analyzed within the food preparation space without affecting the food itself or interfering with the preparation process.

Preferably, the existing central opening of a lid is used for routing through the at least one optical fiber. In particular, a closure is in that case provided for the opening in order to be able to tightly close the opening with the optical fiber routed therethrough. Preferably, the opening is disposed in a container at an upper edge, edge region or upper region of the container. Preferably, a through hole is provided as the opening for routing the optical fiber from the outside into the food preparation space. Preferably, the opening has a cross-sectional area which corresponds to the cross-sectional area of the optical fiber or of two optical fibers, optionally plus the cross-sectional area of a seal, in order to route one or two fibers into the food preparation space in a space-saving and tight manner. Preferably, a seal is provided for sealing the opening with the optical fiber or fibers. In particular, the opening has an inclination relative to the outer surface of the lid or the container in order to analyze a target region in the food preparation space. Preferably, several differently oriented openings or a pivoting device is provided, so that the target region for analysis in the food preparation space can be changed and adjusted particularly flexibly. Preferably, the optical fiber and the opening are configured in such a way that a manual attachment and detachment of the optical fiber in the opening or from the opening is provided. A damaged optical fiber can thus be simply and quickly replaced by the user. Moreover, the optical fiber can thus be inserted only when an analysis is desired, and otherwise, the opening can be closed with a closure. Alternatively or additionally, the optical fiber can be firmly connected to the opening in such a way that this connection is not intended to be disengaged by the user.

In one embodiment, the optical fiber, in particular of the beam source and/or radiation detector, extends through an opening through the tool. This is advantageous in that the optical information is gathered directly from the interior of the food preparation space and not obtained from the outside. Surface effects, such as the skin on a pudding, which would otherwise affect the analytical result, can be eliminated in this way. Preferably, the at least one optical fiber extends through the tool for blending and/or chopping, along the tool axis, to the food preparation space. Centrifugal forces on the optical fiber can thus be avoided. In particular, a rotary bearing and/or a seal are provided in order to route the optical fiber through the tool in a rotationally flexible or tight manner.

In particular, the optical fiber is aligned with an inner contour of the food preparation space, i.e. it does not protrude over an inner container wall or an outer tool contour. Damage to the fiber and fiber residues in the food can thus be avoided particularly effectively. The fiber preferably consists of a biocompatible material.

In one embodiment, an optical coupling interface for connecting the optical fiber to the spectrometer, the beam source, the container, the lid and/or the tool is provided, or, in each case, an optical coupling interface is configured for this purpose. An optical coupling interface permits guiding an excitation radiation or measuring radiation between two optical devices, such as two optical fibers, or between the optical fiber and an optical system for forming an optical path. An optical system for forming an optical path is preferably provided at the output of the beam source and at the input of the spectrometer. In particular, an optical system may be integrated into the container, the lid of the tool in order to affect the food and the preparation process as little as possible and to be able to withstand these conditions with as little wear as possible. In the simplest case, an optical system may be an analysis window. By means of an optical system, a moving device or a focusing device can further be implemented particularly easily.

An optical coupling interface at a part of the tool located outside the food preparation space, in particular on the tool's axis of rotation, makes it possible to transmit the excitation radiation and/or the measuring radiation from the optical fiber into an optical system or a separate section of the optical fiber within the tool, i.e. uncoupled from a rotation of the tool. When the tool rotates, the optical system or the separate section of the optical fiber rotate along with the tool, wherein, nevertheless, the excitation radiation and/or the measuring radiation is transmitted from the optical fiber that is stationary relative thereto. The optical system or the separate section of the optical fiber is non-rotatably connected to the tool in this configuration.

In one embodiment, an optical combiner is provided, which is configured such that the excitation radiation can be guided through the optical fiber and an additional optical fiber, or the measuring radiation can be guided through the optical fiber and an additional optical fiber. An optical combiner is a Y-distribution device. Thus, either can measuring radiation from the optical fiber and the additional optical fiber be guided to the same spectrometer, or excitation radiation from only a single beam source can be guided through the optical fiber and the additional optical fiber. With an optical combiner, it can be made possible that an additional optical fiber can be connected or coupled to the beam source or the radiation detector in addition to the optical fiber. Thus, a food can be analyzed at two different locations. Furthermore, a food can be analyzed within, and a food or a food component outside, the food preparation space, by means of the same beam source and/or the same radiation detector.

In one embodiment, a container with the food preparation space or a lid for the food preparation space has an analysis window. "Analysis window" means a window for analyzing a food within the food preparation space. In particular, the analysis window is largely permeable for the excitation radiation and/or a measuring radiation provided for analysis. A measuring radiation provided for analysis means reflected radiation or transmitted radiation from the food within at least one wavelength range, which is stored in a storage unit for the recognition of a predefined spectral fingerprint. An analysis window is preferably realized in the form of a glass plate. An analysis window allows for a particularly high level of ruggedness of the analysis system and an analysis of the food underneath the surface of the food. An analysis window may be used in addition to or in connection with an optical fiber. An analysis window may also be used as an alternative for an optical fiber. Thus, a fiber can be dispensed with.

In one embodiment, a moving device and/or a focusing device are provided, so that an excitation radiation can be flexibly directed towards a food and/or a measuring radiation from a food can be flexibly captured. "Flexible" means from a different position, under a different angle or with a different focus setting or focal length. In particular, the moving device is capable of moving or inclining a spectrometer, a beam source or an end of an optical fiber. In particular, the focusing device includes a lens system and/or is connected, i.e. optically coupled, to the input of a spectrometer, the output of a beam source, an end of an optical fiber or an analysis panel. By means of a moving device, an analysis can be carried out at different locations of the food, for example by means of an analysis window and/or without using an optical fiber. Regions of the food with different sizes can be analyzed or a particularly precise analysis can be made possible by means of a focusing device. A location-selective analysis is made possible by the moving device and/or focusing device.

In one embodiment, a camera is provided for digitally imaging a food. A camera is an optoelectronic apparatus, in particular for electronically recording a static or moving object in the visible wavelength range of the electromagnetic radiation emanating from the object. "To digitally image" means a conversion into digital image values, e.g. pixel values. By providing a camera, optical clustering, i.e. an object identification, becomes possible. Spatially separate food components, e.g. a potato next to a piece of meat, can thus be recognized, and this information can be included in the analysis. In part, individual predefined food components can also be recognized in one embodiment using the camera and by comparison with stored reference image models.

In one embodiment, the spectrometer and/or the beam source are integrated into or mechanically connected to an oven or a container with the food preparation space, a lid for the food preparation space and/or a basic device for accommodating the container. "Integrated" means permanently installed. The integration allows for a particularly compact design.

In one embodiment, the spectrometer and the beam source are provided as a joint analysis unit and/or can be coupled to an oven, to a container with the food preparation space, to a lid for the food preparation space and/or to a basic device for accommodating the container. "Joint analysis unit" means that the spectrometer and the beam source are permanently connected to each other, i.e. are not intended to be disengaged from each other by the user. By providing the spectrometer and the beam source as a joint analysis unit, the analysis unit can be moved particularly efficiently by only a single moving device. Moreover, a portable use of the analysis unit is supported. "Can be coupled" means that the spectrometer, the beam source or the analysis unit are configured for being manually and mechanically coupled and uncoupled, i.e. detached and removed, by the user. In one embodiment, the spectrometer can be separately removed and used portably. In another embodiment, the beam source can be separately removed and used portably. The portable use is advantageous in that a prepared food or a food component to be added can be analyzed outside the food preparation space, for example.

In one embodiment, the spectrometer, the beam source or the analysis unit can be mechanically permanently connected to an oven, container or basic device for accommodating the container, i.e., the mechanical connection is not configured to be manually disengaged by the user. This simplifies the measurement signal connection and power supply. Alternatively or additionally, the mechanical connection is configured as a permanent connection, but can be oriented flexibly, for example in order to be able to analyze a food both within and outside the food preparation space. In particular, the mechanical connection or coupling is carried out in an upper region or an upper edge of a container. A spectrometer and/or beam source integrated into the lid or an intermediate lid attachment can be frictionally or positively connected to an upper edge of a container in one embodiment.

In one embodiment, the food preparation device is configured such that, prior to preparing a food, a food component for the food to be prepared is analyzed, or the food is analyzed in the state prior to preparation. "Prior to preparation" means prior to blending, chopping and/or heating in the food preparation space. Thus, an optimization of the cooking process based on the analysis of the food or food components prior to preparation and a reproducible cooking result can be obtained.

In particular, prior to preparation, a food component is analyzed outside the food preparation space, and/or a food component yet to be added is analyzed outside the food preparation space. In this way, particularly accurate knowledge of the actually used ingredients or food components to be added, and thus the nutritional value of a self-prepared food, can be obtained, e.g. for adhering to a diet. So far, specifications for nutritional values in recipes for self-prepared foods could only be roughly estimated based on generic data of the ingredients or tests from the trial period of the recipe. So far, a variation or even substitution of the introduced ingredients, i.e. the food components to be added, could not be modeled. Neither are the actually used ingredients taken into account so far.

In particular, the food or the food components are analyzed in the food preparation space prior to preparation. Thus, the cooking process can be adapted to a variable quantity or quality of the initial state of the food prior to preparation, or of the introduced food components, in order to obtain a reproducible or at least optimized cooking result even in the case of changed mixing ratios, recipe changes or foods prepared without a recipe.

In one embodiment, the food preparation device is configured such that, during the preparation of a food, the food or a food component of the food is analyzed. The analysis takes place within the food preparation space. A dynamic adaptation and/or control of the preparation parameters, such as temperature, cooking time or rotation speed of the tool can thus take place depending on the identified food components, the currently present ingredient substances and the actual state of the food. Furthermore, a dynamic adaptation of the list of ingredients can be carried out and indicated to the user during the preparation if a lack or excess of a specific ingredient substance is detected. A particularly optimized and/or reproducible cooking result can thus be made possible in spite of variable quality and quantity of the initially added food components, i.e. foodstuffs or ingredients, and changes to the food components during preparation, e.g. due to evaporation or fermentation. A destructive or, especially, invasive analysis and a resulting interference with the preparation process by the analysis itself can also be avoided.

If the target value of a predefined monitoring quantity has been reached, the food preparation device can take correspondingly predefined measures stored in a storage unit. For example, when cooking or baking, the browning level may be the monitoring quantity, and the desired browning level the target value, so that a heating element is switched off or turned down when the target value has been reached. If the desired browning level has not been reached yet, but the desired core temperature of the food, i.e. in this case of the product to be cooked, has already been reached, an oven as the food preparation device may be operated in the grill mode, for example, in order to quickly achieve external browning. If the desired browning level has been reached, but not yet the desired core temperature of the food, the temperature can be turned down or the user can be requested to cover the food.

In one embodiment, food-specific or user-specific stopping or abort criteria are defined. Thus, for example, a cooking process can be stopped if the analysis determines that a predetermined browning level has been reached. Moreover, in a further embodiment, a safety function can thus be implemented, which aborts the preparation process when a predetermined alcohol concentration has been reached, for example, during the distillation of alcohol in a food processor or another kitchen appliance.

In one embodiment, the food preparation device is configured such that the food is analyzed after the preparation of a food. Thus, the user receives accurate information about the actual nutritional value of the prepared food independent of deviations from the recipes and his own creations. A quick, non-destructive and uncomplicated nutritional value analysis of a self-prepared dish can be realized. By analyzing the actual state of the food prior to eating, it is made possible for the user to adhere to a diet plan particularly reliably. Estimating, weighing and manual calculation using nutritional value tables can be completely dispensed with. In one embodiment, a link to a food processor is created for optimizing stored cooking parameters for a specific food or for taking into account, for nutritional value analysis, the recipe used and provided by the food processor in order to obtain a particularly high precision of the analytical result. If in one embodiment, the diet plan is stored in a control device, a target/actual comparison may take place and, for example, displayed by a food processor. Preferably, the food is analyzed within the food preparation space in order to be able to carry out the analysis in a fully automated manner particularly easily, subsequent to the adding process. Alternatively or additionally, an analysis of the food outside the food preparation space is also possible.

In one embodiment, a control device with a processor unit and a storage unit is provided. In particular, the control device is configured such that a method can be carried out using the processor unit, preferably based on a computer program or commands stored in the storage unit. The stored data, i.e. at least one data set, reference value and/or reference image model, are preferably stored in the storage unit, i.e. digitally stored. The, in particular, analog and/or digital measurement signals of the spectrometer and, optionally, of a camera can be processed by the control device. Preferably, signal preprocessing and/or signal correction, e.g. for compensating a temperature influence or for analog/digital conversion, are being carried out before the preprocessed measurement values thus obtained are analyzed using the stored data, particularly while applying predefined algorithms. Since there are frequently elevated temperatures during the preparation process, which are also reflected in an amount of infrared radiation, a temperature measurement is provided in one embodiment, which is preferably carried out by an existing temperature sensor of, for example, a food processor or oven. The influence of the temperature can then be eliminated, e.g. by means of its Planck curve. In particular, the control device is integrated into the main device. Complete or partial outsourcing of the control device and/or the storage unit with the data sets, reference values and/or reference image models into a cloud is provided in an alternative or additional embodiment. In particular, the cloud is connected to a basic device of the food preparation device for the exchange of data. "Into a cloud" means storing data and/or processing data by a remote computer which is accessible, for example, via the internet. In one embodiment, this computer is capable of sending back control commands.

In one embodiment, a spectral fingerprint is stored in the form of a data set, which is assigned to a certain food, a certain food component, a certain property or a certain state. Preferably, this data set, for one or more predefined wavelengths of the measuring radiation, respectively includes one predefined intensity threshold or one predefined intensity range. If a comparison of the measuring radiation to the data sets shows that the conditions of a certain data set are met by the measuring radiation, the food, food component, property or state of the recognized spectral fingerprint or of the correspondingly assigned data set is outputted as the analytical result. Foodstuffs, ingredient substances and states can thus be identified based on their spectral fingerprint. In particular, an analytical result may be a browning level, an alcohol concentration, a water content, a cocoa content in a chocolate, a gluten content in flour, a main nutrient content or an energy content. The analytical result may be both a qualitative presence of an ingredient substance and its quantitative concentration. The identification of a food component, e.g. "apple", is also possible. In particular, a particularly precise analysis can be achieved by means of a database comparison or by taking into account the recipe or the cooked food, wherein this information can be provided to the control device, for example, by a food processor or a smartphone.

In one embodiment, an analytical result is communicated to the user via an output by the food preparation device, in particular, visually, acoustically or by means of a transmission to an external device, such as a smartphone. Depending on the analytical result, a food processor can, in particular, output a recommendation to the user depending on the recipe. If, for example, the sugar level recommended for a particular flavor has not yet been reached due to ingredients that are too sour, sweetening can be recommended to the user.

In one embodiment, the spectrometer and/or the beam source are connected to the control device and/or food preparation device via a wired or wireless interface, in order to exchange measurement signals and control signals. Preferably, the control device is connected to a food processor, and the food processor to an oven, for exchanging data.

Another aspect of the present disclosure relates to a method for analyzing a food, wherein the food or a component of the food or food component is analyzed by means of a spectrometer, prior to, during and/or subsequent to a preparation of the food, wherein the preparation of the food is carried out by means of a food preparation device comprising a food preparation space and a heating element for heating a food in the food preparation space and/or a tool for blending and/or chopping a food in the food preparation space. In particular, the food preparation device is the food preparation device according to the aspect of the present disclosure described in the introduction, so that the above-described features and embodiments can be combined with the method.

Exemplary embodiments of the present disclosure will be explained below in more detail with reference to Figures. Disclosed features may be combined in any way with the subject matters for which protection is sought. The claimed scopes of protection are not limited to the exemplary embodiments.

BRIEF DESCRIPTIONS OF THE DRAWINGS

Figure 1:
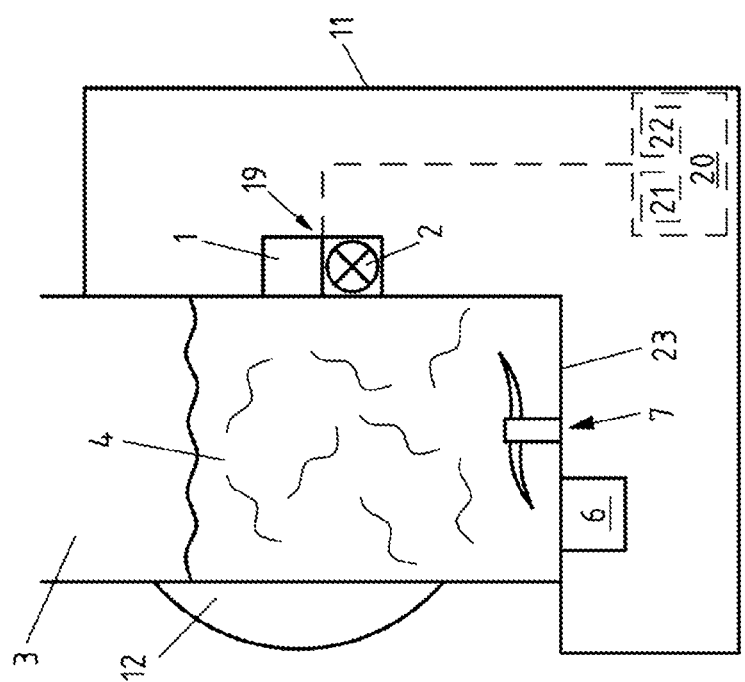

In the Figures:

FIG. 1: shows a schematic representation of a food preparation device with a spectrometer;

FIG. 2: shows a schematic representation of a food preparation device with a spectrometer and optical fibers that can be used in a flexible manner;

FIG. 3: shows a schematic representation of a food preparation device with a spectrometer and optical fibers through the tool for blending and/or chopping;

FIG. 4: shows a schematic representation of a food preparation device with a spectrometer and an analysis window;

FIG. 5*a*: shows schematic representation of a variant of the arrangement of a spectrometer and a beam source in the food preparation space side-by-side above a food;

FIG. 5*b*: shows schematic representation of a variant of the arrangement of a spectrometer and a beam source in the food preparation space side-by-side underneath a food;

FIG. 5*c*: shows schematic representation of a variant of the arrangement of a spectrometer and a beam source in the food preparation space with a heating element as a beam source;

FIG. 5*d*: shows schematic representation of a variant of the arrangement of a spectrometer and a beam source in the food preparation space with a camera (spectrometer and beam source are hidden);

FIG. 5*e*: shows schematic representation of a variant of the arrangement of a spectrometer and a beam source in the food preparation space with a moving and focusing device (spectrometer and beam source are hidden);

FIG. 5*f*: shows schematic representation of a variant of the arrangement of a spectrometer and a beam source in the food preparation space with the beam source above and the spectrometer underneath the food;

FIG. 5*g*: shows schematic representation of a variant of the arrangement of a spectrometer and a beam source in the food preparation space with the beam source and the spectrometer at two opposite end regions of an upper boundary of the food preparation space; and FIG. 5*h*: shows schematic representation of a variant of the arrangement of a spectrometer and a beam source in the food preparation space with the beam source and the spectrometer at two opposite side walls of an upper boundary of the food preparation space.

DETAILED DESCRIPTION

FIG. 1 shows a food preparation device with a spectrometer 1 and a beam source 2, which, as an analysis unit 19, is preferably connected or connectable to the container 12 with the food preparation space 3 for a food 4 or the basic device 11 of the food preparation device. A tool 7 and a heating element 6 serve for preparing the food 4. A control device 20 with a processor unit 21 and a storage unit 22 is connected to the spectrometer 1 and/or the beam source 2. In one embodiment, the analysis unit 19 is configured as a portable handheld device, which the user can point at a food to be examined for analysis. Preferably, however, the analysis unit 19 is firmly connected to the food preparation space 3, i.e. the container 12, a pot or oven space, e.g. by means of an optical analysis window and/or an optical fiber, as described below. The bottom of the container 12 forms the supporting means 23 for the food 4. If the analysis unit is configured as a portable handheld device, the analysis unit may, in principle, be retained by a bracket of the food preparation device in such a way that desired analyses can be carried out without having to manually support the analysis 19 for this purpose.

FIG. 2 shows a food preparation device in which an excitation radiation is guided from the beam source 2 via an optical fiber 8 into the food preparation space 3, and a measuring radiation is guided back to the spectrometer 1 by a second optical fiber 8, in particular through a lid 13 in each case. In particular, an optical combiner 14, i.e. a Y-distribution device, is provided in order to couple an additional optical fiber 9 to the beam source 2 and/or the spectrometer 1, respectively. A food component 5 outside the food preparation space 3 can this also be analyzed by a firmly integrated spectrometer 1.

FIG. 3 shows a food preparation device in which the optical fibers 8 of the beam source 2 and/or of the spectrometer 1 extend through the tool 7 for blending and/or chopping to the food preparation space 3, particularly along the tool axis. A coupling interface 10 is preferably provided in order to obtain an optical transmission of the excitation radiation and/or measuring radiation without motion coupling, so that the tool is able to rotate without the optical fibers 8, which are coupled to the beam source 2 and/or the spectrometer 1, rotating along.

FIG. 4 shows a food preparation device with an analysis window 15 for transmitting the excitation radiation and/or measuring radiation between the food preparation space 3 and the beam source 2 or the spectrometer 1. Preferably, the analysis window 15 is scratch-resistant, impact resistant, temperature resistant and/or provided with a heat expansion coefficient similar to that of the surrounding container wall. In one embodiment, the analysis window 15 extends, as shown in FIG. 4 by dashed lines, from a lower edge region or region of the container to an upper edge region or region of the container. The analysis unit 19 can be driven along the analysis window 15 by means of a moving device 16 in order to analyze the food 4 at different positions.

FIG. 5 shows different variants of the arrangement of a spectrometer 1 and a beam source 2 in the food preparation space 3, which is preferably provided by a food processor or an oven. In the FIGS. 5a, 5b and 5c, the spectrometer 1 and the beam source 2 are disposed close to each other or adjacent to each other. In the FIGS. 5a and 5c, the food 4 is analyzed from above. In FIG. 5b and an alternative of FIG. 5c (shown in dashed lines), the food 4 is analyzed from below through an optically transparent supporting means 23, e.g. a transparent disk or grid, which permits providing a defined distance from the food. In one embodiment, as shown in FIG. 5c, the spectrometer 1, the beam source 2 and/or the heating element are directly connected to the supporting means 23. In the exemplary embodiment of FIG. 5c, a heating element 6 is used as a beam source 2. The heating element 6 is preferably a thermoelectric element of a food processor or a heating rod of an oven. FIG. 5d shows a camera 18 in addition to a spectrometer 1 and a beam source 2, which are both hidden in FIG. 5d. In FIGS. 5a to 5d, the reflected radiation is used as the measuring radiation for analysis, in particular with an acute angle between the excitation radiation and the measuring radiation. FIG. 5e illustrates a moving device 16 for translationally moving and rotationally inclining a spectrometer 1. Alternatively or additionally, the moving device 16 may also be used for the beam source 2 or an analysis unit 19. A focusing unit 17 enables a particularly target-specific acquisition of measuring radiation from the food 4 and/or emission of excitation radiation towards the food 4. FIG. 5f shows the arrangement for the analysis of a transmitted radiation as the measuring radiation, whereas FIGS. 5g and 5h illustrate arrangements for the analysis of a reflected radiation measured at a particularly large angle of incidence and reflection of less than 60° relative to the supporting means 23 of the food 4.

The invention claimed is:

1. A food preparation device comprising
a food preparation space,
a heating element configured to heat a food in the food preparation space,
a tool configured to blend or chop the food in the food preparation space,
a spectrometer in communication with the food preparation space and configured to analyze the food in the food preparation space,
a beam source configured to emit infrared radiation and analyze the food, and
an optical fiber configured to guide a measuring radiation between the food and the spectrometer and an excitation radiation between the beam source and the food,
wherein the optical fiber is formed to extend from outside the food preparation space through an opening in a container formed to define the food preparation space, through a lid configured to be positioned above the food preparation space and into the food preparation space,
wherein the spectrometer and the beam source are located outside the food preparation space.

2. The food preparation device according to claim 1, wherein the spectrometer and the beam source are provided as a joint analysis unit and are configured to be coupled to an oven, to a container defining the food preparation space therein, and to a basic device configured to accommodate the container.

3. The food preparation device according to claim 2, wherein the food preparation device is configured to analyze a food component for the food prior to preparing the food.

4. The food preparation device according to claim 3, wherein the food preparation device is configured to analyze the food during preparation.

5. The food preparation device according to claim 3, wherein the food preparation device is configured to analyze the food subsequent to the preparation of the food.

6. A food preparation device comprising
a food preparation space,
a heating element configured to heat a food in the food preparation space,
a tool configured to blend or chop the food in the food preparation space,
a spectrometer in communication with the food preparation space and configured to analyze the food in the food preparation space,
a beam source configured to emit infrared radiation and analyze the food,
an optical fiber configured to guide a measuring radiation between the food and the spectrometer and an excitation radiation between the beam source and the food, and
an optical combiner configured to guide the excitation radiation or the measuring radiation through the optical fiber and a second optical fiber, and the second optical fiber configured to guide the measuring radiation between a food component and the spectrometer and an excitation radiation between the beam source and the food component, wherein the food component is outside the food preparation space.

7. A food preparation device comprising,
a food preparation space,
a food processing device for interaction with food in the food preparation space, the food processing device including a heating element configured to heat a food in the food preparation space and a tool configured to blend and chop the food in the food preparation space, and
a spectrometer configured to analyze food present in the food preparation space, wherein the food processing device is configured to adjust operation based at least in part on analysis from the spectrometer related to the food present in the food preparation space,
wherein the food processing device is configured to individually adjust the heating element and the tool in response to the analysis from the spectrometer to optimize the food preparation process.

8. The food preparation device according to claim 7, further including a beam source configured to emit infrared radiation and analyze the food.

9. The food preparation device according to claim 8, further including an optical fiber configured to guide an excitation radiation between the beam source and the food.

* * * * *